(12) United States Patent
Sezginer et al.

(10) Patent No.: US 7,095,496 B2
(45) Date of Patent: Aug. 22, 2006

(54) METHOD AND APPARATUS FOR POSITION-DEPENDENT OPTICAL METROLOGY CALIBRATION

(75) Inventors: Abdurrahman Sezginer, Los Gatos, CA (US); Kenneth Johnson, Santa Clara, CA (US); Adam E. Norton, Palo Alto, CA (US); Holger A. Tuitje, Fremont, CA (US)

(73) Assignee: Tokyo Electron Limited, Tokyo (JP)

( * ) Notice: Subject to any disclaimer, the term of this patent is extended or adjusted under 35 U.S.C. 154(b) by 219 days.

(21) Appl. No.: 10/317,898

(22) Filed: Dec. 12, 2002

(65) Prior Publication Data

US 2003/0147070 A1 Aug. 7, 2003

Related U.S. Application Data

(60) Provisional application No. 60/369,475, filed on Apr. 2, 2002, and provisional application No. 60/339,628, filed on Dec. 12, 2001.

(51) Int. Cl.
*G01N 21/88* (2006.01)

(52) U.S. Cl. ............ 356/241.1; 356/394; 356/237.2

(58) Field of Classification Search ... 356/241.1–241.6, 356/243.1, 234.4, 394, 445, 244, 237.1, 237.2, 356/237.3, 237.4; 250/252.1, 491.1; 438/14–16
See application file for complete search history.

(56) References Cited

U.S. PATENT DOCUMENTS

| | | | | |
|---|---|---|---|---|
| 3,999,866 A | * | 12/1976 | Mathisen | 356/244 |
| 4,046,474 A | * | 9/1977 | Lee | 355/43 |
| 4,386,850 A | * | 6/1983 | Leahy | 356/243.1 |
| 5,004,340 A | * | 4/1991 | Tullis et al. | 356/243.6 |
| 5,129,724 A | * | 7/1992 | Brophy et al. | 356/503 |
| 5,144,363 A | * | 9/1992 | Wittekoek et al. | 355/53 |
| 5,144,524 A |   | 9/1992 | Tullis et al. | 362/293 |
| 5,321,495 A |   | 6/1994 | Hagiwara et al. | 356/237 |
| 5,355,212 A | * | 10/1994 | Wells et al. | 356/237.4 |
| 5,383,018 A | * | 1/1995 | Sadjadi | 356/243.4 |
| 5,486,701 A | * | 1/1996 | Norton et al. | 250/372 |
| 5,502,564 A | * | 3/1996 | Ledger | 356/503 |
| 5,889,593 A | * | 3/1999 | Bareket | 356/445 |
| 6,078,042 A | * | 6/2000 | Fellows | 250/252.1 |
| 6,384,408 B1 | * | 5/2002 | Yee et al. | 250/252.1 |
| 6,405,101 B1 | * | 6/2002 | Johanson et al. | 700/218 |
| 6,563,586 B1 | * | 5/2003 | Stanke et al. | 356/445 |
| 6,743,646 B1 | * | 6/2004 | Jakatdar et al. | 438/16 |
| 6,771,374 B1 | * | 8/2004 | Rangarajan et al. | 356/445 |

FOREIGN PATENT DOCUMENTS

| | | |
|---|---|---|
| JP | 64-30242 | 2/1989 |
| JP | 2-47823 | 2/1990 |
| JP | 4-158540 | 6/1992 |

* cited by examiner

*Primary Examiner*—Gregory J. Toatley, Jr.
*Assistant Examiner*—Sang H. Nguyen
(74) *Attorney, Agent, or Firm*—Stallman & Pollock LLP

(57) ABSTRACT

A calibration method suitable for highly precise and highly accurate surface metrology measurements is described. In preferred embodiments, an optical inspection tool including a movable optics system is characterized in terms of position and wavelength dependent quantities over a range of motion. Once the position-dependant quantities are determined at various wavelengths and positions, they are stored and used to interpret data from test wafers having an unknown metrology. Free of position-dependent variations and other information pertaining to the measurement system, the accuracy of the resulting wafer measurement more closely matches the precision of the tool than existing techniques. In particular embodiments, a portion of the characterization of the optical system is accomplished by using tilted black glass to provide a non-reflective reference.

21 Claims, 11 Drawing Sheets

METHOD AND APPARATUS FOR POSITION-DEPENDENT OPTICAL METROLOGY CALIBRATION

CROSS REFERENCE TO RELATED APPLICATIONS

This application claims priority to, and hereby incorporates by reference the entirety of, applications No. 60/339,628, filed Dec. 12, 2001, and No. 60/369,475, filed Apr. 2, 2002.

FIELD OF THE INVENTION

This invention relates to the field of metrology, and more particularly to optical metrology calibration.

BACKGROUND OF THE INVENTION

There is considerable interest across several industries in developing metrology systems for precisely and accurately measuring physical properties of surfaces, and thin films deposited on surfaces. Optical techniques are often preferable because they can be performed during a manufacturing process without contacting a test article. Typically, an apparatus measures light before and after interacting with a test surface. Surface properties may then be inferred according to a theory of the interaction and an understanding of the operating principles of the apparatus.

To be useful, a metrology system must be precise as well as accurate. Precision refers to a capability to make fine measurements. Accuracy, in contrast, refers a difference between a value obtained from measurement and a true value of the physical property being measured. Generally, a highly precise system is not necessarily highly accurate.

Obtaining high accuracy typically requires understanding system characteristics both theoretically and through calibration. In many applications, however, detailed characterization of the entire measurement system is difficult, or impractical, or simply unwarranted by the desired accuracy of the measurement. Thus, high precision measurements are often not as accurate as they could be because a user interprets a measured signal with a technique that simplifies the operating principles of the measuring apparatus.

Two trends in the semiconductor industry point to a need for improved calibration techniques. First, there is an ever-present trend toward higher measurement accuracy arising from demands for thinner films and more stringent process standards. For example, the currently recommended upper bound on uncertainty in reflectivity measurements is 0.1%.

Second, there is an important trend toward integrating process and metrology tools by locating metrology tools closer to manufacturing process lines. Presently, most metrology systems "stand alone," physically removed from the process tools. Away from the process line, space is not at an economic premium. Accordingly, most "stand-alone" metrology systems opt for immovable optical heads and motion stages that move a test article under the optics. Fixed to a massive frame, the optical systems of stand-alone devices are stable over long periods of time. In contrast, integrating metrology and process tools drives designs having movable optics because space is at a premium near the process line and movable optics significantly reduce the size of a metrology device's "footprint." As compared to fixing the optical head and moving the test article, however, moving the optical head over the test surface requires closer attention to the manner and frequency of calibration because of the movements.

Two examples of common approaches to calibration illustrate the technical problem addressed by this invention. One simple calibration method regards that a signal S relates to a physical quantity of interest Q by:

$$S = \alpha Q \qquad \text{(Eqn. 1)}$$

In Eqn. 1, $\alpha$ contains information from the measurement system and Q is the physical quantity of interest. With this simple relationship between the signal and the quantity of interest, one can remove the information relating to the measurement system and arrive at a relative determination of Q by taking the ratio of two independent measurements $$\frac{S_2}{S_1} = \frac{Q_2}{Q_1} \qquad \text{(Eqn. 2)}$$

Comparing the two equations, above, the factor $\alpha$ dropped out in Eqn. 2. Thus, if a relative determination of the desired quantity suffices for the purposes of the measurement, it is not necessary to know the characteristics of the measurement system embodied in the factor $\alpha$, including any position-dependencies.

U.S. Pat. No. 5,747,813 exemplifies the approach, above, by teaching a method for determining a relative reflectance of a wafer with dual beam reflectometer. See col. 2, lines 31–41. In U.S. Pat. No. 5,747,813, knowledge about the reflectometer characteristics, such as optical efficiencies, detector gains and noise is not necessary to arrive at a relative reflectivity of the wafer. Such information "drops out" because of the ratio, above. Relative reflectivity is useful, for example, in monitoring process consistency on a wafer-to-wafer basis. For an absolute determination, U.S. Pat. No. 5,747,813 teaches further use of ratios to reference to a known standard. See col. 2, lines 31–41.

Relative measurements are simple, convenient and adequate for some uses. Often, however, a measurement system behaves in a more complicated manner than Eqn. 1 suggests. For example, one may interpret a signal S as relating to a physical quantity of interest Q by:

$$S = \alpha Q + \beta \qquad \text{(Eqn. 3)}$$

In Eqn. 3, $\alpha$ and $\beta$ both relate to the measurement system. Comparing Eqn. 3 to Eqn. 1, just one additional factor, $\beta$, disallows simply forming a ratio from two experiments to remove the information about the measurement system. The factors relating to the measurement system simply do not drop out from a ratio.

In curve fitting, one presupposes a mathematical form of a family of curves and determines coefficients that fit data points "best." Common mathematical forms include polynomials, often with many terms. FIG. 1 illustrates the curve fitting approach. FIG. 1 includes data points 100, and curves 110–130. The data points represent signal values at a corresponding value of the physical quantity of interest. The different curves are for different possible mathematical forms that "fit" the data.

FIG. 1 shows that many different orders of polynomials "fit" the data, even when there is no position dependence. This is a drawback in that a range of curves that fit the data is an uncertainty that may limit the accuracy of a measurement. If the range of curves is substantial compared to the desired accuracy of the measurement (0.1% or less in the semiconductor industry), a more rigorous interpretation of the data is useful, if not essential. Moreover, with moving optics, the calibration problem is significantly complicated because of position-dependencies.

Therefore, because of new demands for movable optical systems with position-dependent characteristics and a continuing broad demand for greater accuracy, there is a need for calibration techniques and associated components that enable detailed, position-dependent characterization of a metrology system.

SUMMARY OF THE INVENTION

The present invention is a calibration method and related apparatus that are suitable for highly precise and highly accurate surface metrology measurements. In a typical measurement, a wafer inspection tool with a polychromatic light source generates a probe beam, which illuminates a sample. A detector measures the probe beam after reflection from the sample. The inspection tool includes an optics system for directing the probe beam onto the sample, with the optics system being movable over the wafer to scan measurement points on the wafer.

In a preferred embodiment, a calibration wafer is measured over a range of different wavelengths at each of a plurality of different positions of the optics system. Then, variations in measurement parameters at a plurality of discreet wavelengths are determined. The variations are a direct result of moving the optics system. After determining and storing position and wavelength related calibration information based on such variations, the calibration information can be used to correct for position variations of the optics system when measuring a test wafer.

In another preferred embodiment, a portion of an optical metrology apparatus moves over a plurality of positions relative to a test article holder, changing a measurement location over the test article holder. Then, calibration signals over the plurality of positions with the optical metrology apparatus are produced. At each position, the calibration signals contain information over a range of wavelengths. By comparing the calibration signals to a model of signals produced by the metrology apparatus including a set of position-dependant parameters characterizing the optical metrology apparatus, one determines values for the position-dependant parameters at a plurality of discreet wavelength values. With values for the position-dependant parameters, other data from wafers with unknown metrology can be determined.

In these and other preferred embodiments, a portion of the calibration involves placing a reference element in an optical path of a probe beam such that specular reflections of the probe beam off of a surface of the reference element are directed outside the collection angle. Light relating to a background light level is then sensed with a detector of the metrology apparatus. The reference element is preferably black glass. Other reflective materials are also possible. In different embodiments, such reference elements may be coupled to a wafer, or a chuck, or another support structure. In still other embodiments, a plurality of elongated reference elements of differing reference characteristics are coupled to the chuck, thereby, providing a unitary calibration structure with a range of reference characteristics that may be sequentially scanned over the range of motion of the movable optics system.

One example of the use of a reference element in association with a chuck is disclosed in U.S. patent application Ser. No. 2002/0159054, assigned to the same assignee as herein and incorporated by reference.

DETAILED DESCRIPTION OF THE PREFERRED EMBODIMENTS

I. Calibration Method

The present invention is a calibration method suitable for highly precise and highly accurate surface metrology measurements. In preferred embodiments, an optical inspection tool including a movable optics system is characterized in terms of position-dependent quantities over a range of motion. Once the position-dependant quantities are determined, they are stored and used to interpret data from test wafers having an unknown metrology. Free of position-dependent variations and other information pertaining to the measurement system, the accuracy of the resulting wafer measurement more closely matches the precision of the tool than existing techniques.

To calibrate a tool according to a preferred embodiment, at least one calibration sample is measured at each of a plurality of different positions of the movable optics system. Characteristic quantities of the tool and their position dependence are then determined by comparing the calibration data to a computational model of signals produced by the calibration samples and the measurement instrument. The model of signals may depend linearly or non-linearly on the reflectance of the sample, depending on the desired accuracy and complexity of the tool's operation. In some preferred embodiments, an over determined system of equations result from comparing the measurements on a multitude of calibration samples to the model of signals. The tool's operating characteristics are determined by solving the system of equations at the discreet wavelengths and positions of the movable parts of the instrument. Once the tool's behavior is determined at the discreet positions and wavelengths, one may infer behavior over a continuous range by interpolation or curve fitting.

Embodiments with a dual beam optical system for determining surface reflectivity are convenient for illustration purposes. No limitation to such a system, however, is implied. Alternate embodiments include but are not limited to: single beam reflectometers, such as in U.S. patent application Ser. No. 10/290,730, filed Nov. 7, 2002 which is herein incorporated in its entirety by reference; reduced polarization spectrometers, such as in U.S. patent application Ser. No. 2002/0021441, published Feb. 21, 2002, which is herein incorporated in its entirety by reference;

ellipsometers, scatterometers; and profilometers. Likewise, while particular embodiments of chucks and calibration articles are described below for illustration purposes, no limitation to such embodiments is implied.

Figure 1:
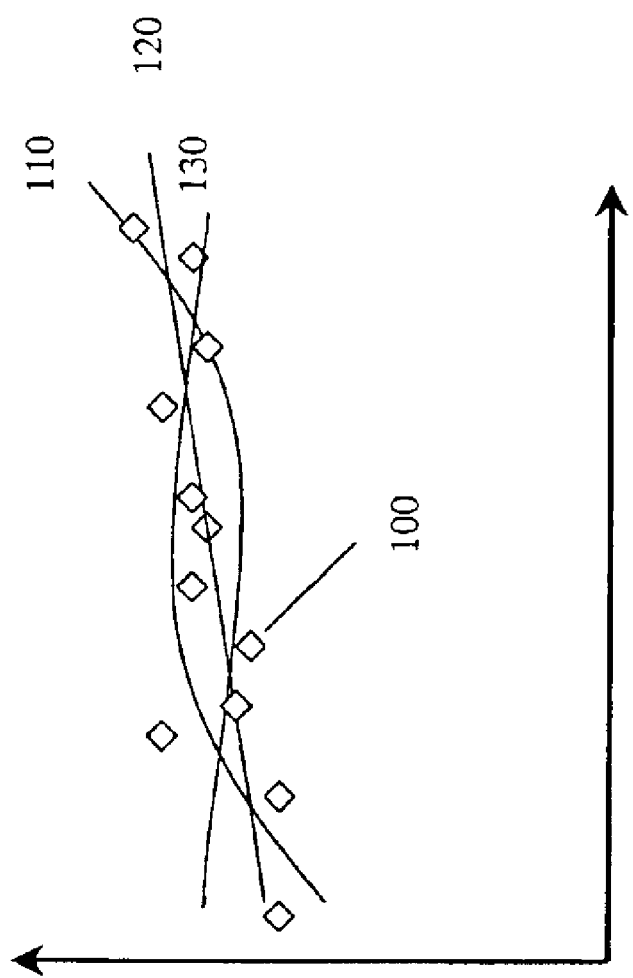
FIG. 1 illustrates results of the curve-fitting technique.
Figure 2A:
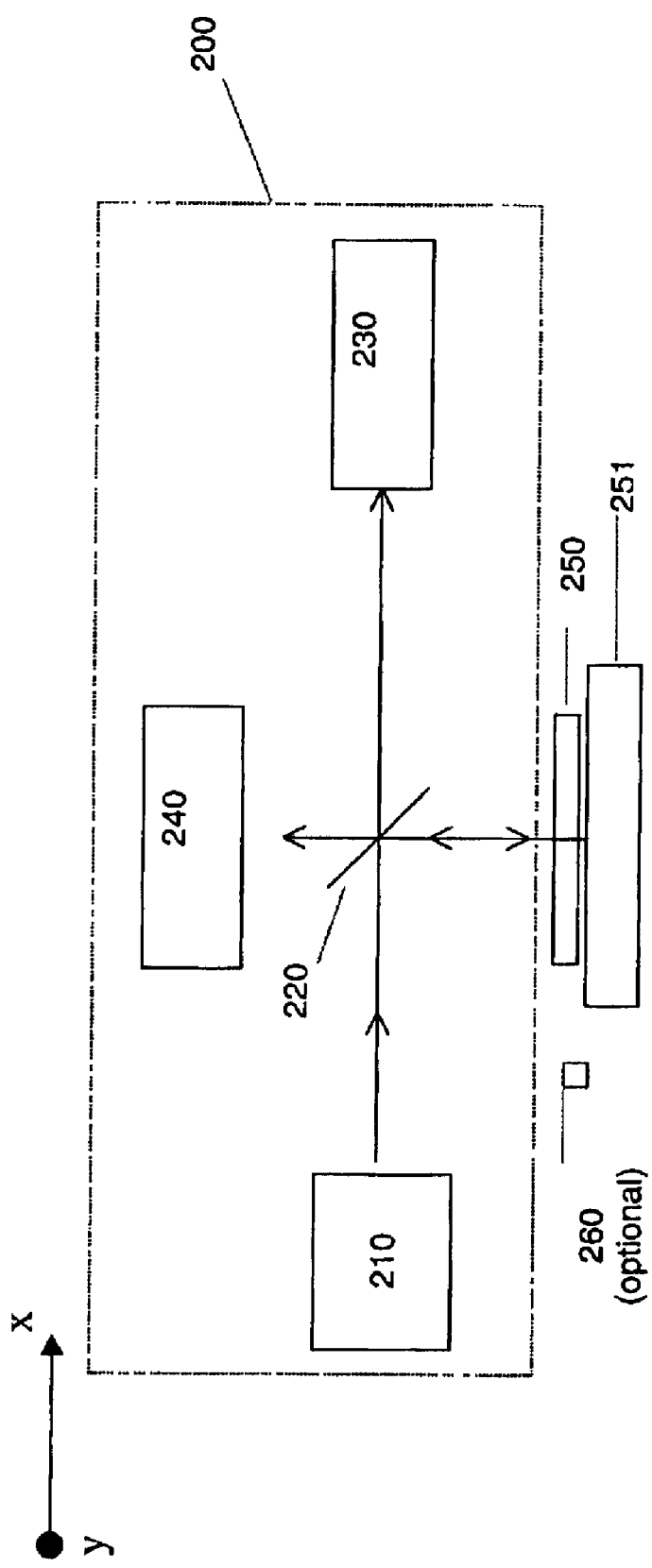
FIG. 2 illustrates two dual beam reflectometers with movable optical heads.

FIG. 2 illustrates aspects of dual beam reflectometer embodiments that include a movable optical system. FIG. 2a shows movable optical system 200 comprising light source 210, beam splitter 220, light source monitoring detector 230, reflected light detector 240, reference reflector 260, test article 250, and chuck 251. It is noteworthy that in the following, "test article" and "sample" are used synonymously. For clarity, FIG. 2a omits other elements such as fiber optics, lenses and relay mirrors that may be present in an actual system.

Figure 6:
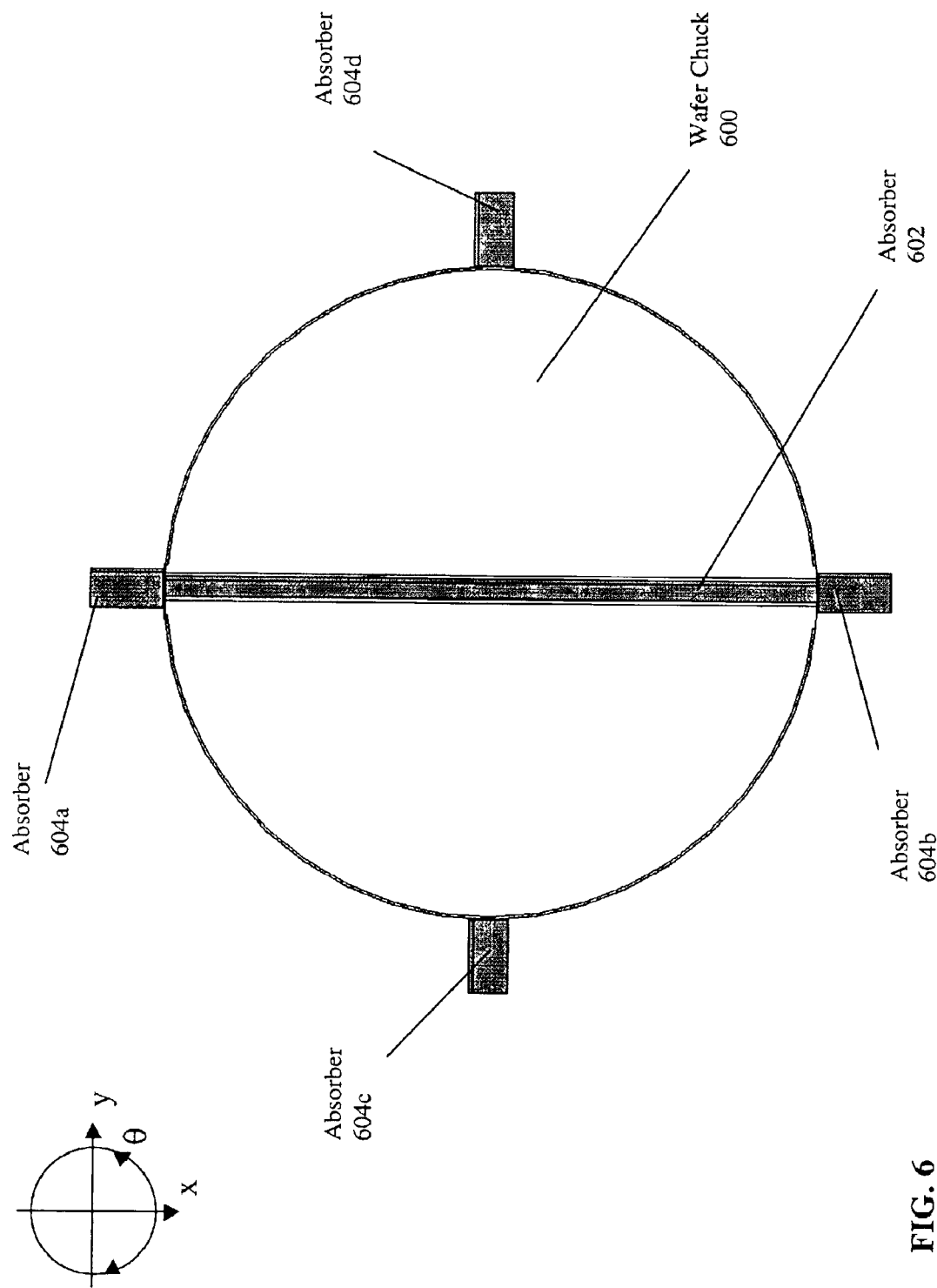
FIG. 6 illustrates a preferred embodiment of a chuck with non-reflective portions.

In FIG. 2a, optical system 200 is movable through a range of measurement positions over reflective surface 250. In alternative embodiments, however, the optical system is fixed. Chuck 251 supports the reflective surface. In a preferred embodiment, the chuck is rotatable and includes calibration references pieces. See FIG. 6 and discussion below. In alternative embodiments, the chuck does not rotate. In yet other embodiments, the chuck does not include a calibration reference piece. Again referring to FIG. 2a, some embodiments of the optical system optionally account for slow drifts in detector gains by making measurements of reference reflector 260. The reference reflector, when included, has a reflectivity that is extremely stable over time. Particular embodiments of the reference reflector have a layer of chrome sandwiched between quartz plates.

Figure 2B:
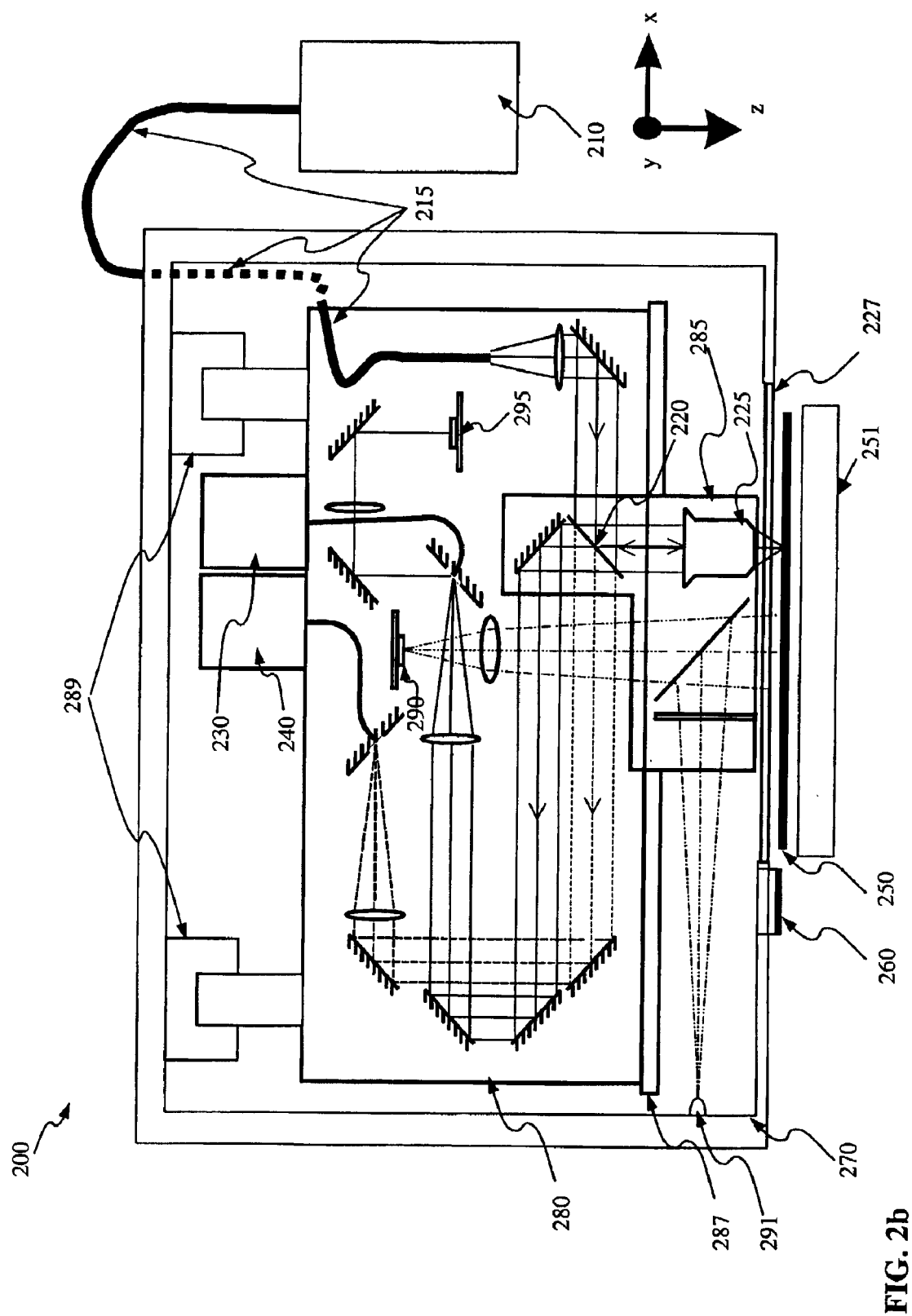

FIG. 2a omits elements for the sake of clarity. FIG. 2b shows a particular embodiment of a dual beam reflectometer with a movable optical system in detail. See U.S. patent application Ser. No. 2002/0018217, published Feb. 14, 2002, the entirety of which is hereby incorporated by reference. Similarly to FIG. 2a, FIG. 2b shows movable optical system 200, light source 210, beam splitter 220, light source monitoring detector 230, reflected light detector 240, reference reflector 260, test article 250, and chuck 251. Further, light source fiber optic 215, auto-focusing objective 225, window 227, optical head 285, enclosure 270, light emitting diode 291, x translation means 287, y translation means 289, measurement optics 280, large field of view camera 290, and small field of view camera 295 are shown.

Referring to FIG. 2b, movable optical system 200 includes optical head 285 and measurement optics 280. The optical head is coupled to x translation means 287, which is coupled to the measurement optics. Thus, the optical head is controllably positionable along the x-axis shown in the figure. Further, the measurement optics are coupled to y translation means 289. Thus, the optical head is also controllably positionable along the y-axis shown in the figure. With two independently controllable degrees of freedom, the entire surface of test article 250 is optically accessible through window 227. Alternately, other embodiments include a rotating chuck 251 to hold the test article. In these embodiments, the translation of the optical head along one axis, and the rotation of the chuck through an angle provide a (r,θ) system for optically accessing the entire surface of the test article. To locate the system over a desired measurement position, large field of view camera 290 and small filed of view camera 295 provide images to an operator or pattern recognition system (not shown) with light emitting diode 291 providing illumination primarily for the large field of view camera. The small field of view camera images an area including the area under measurement through auto-focusing objective 225.

FIG. 2 illustrates the freedom of movement of the movable optical system 200 over test article 250. As described above, many prior art devices fix an optical system to a massive frame for stability, and move the test article instead. When, as in FIG. 2a–b, the optics move over the test article, characteristics of the system become position-dependent due to a number of mechanisms. For example, as the apparatus shown in FIG. 2b moves in the y-axis direction, light source fiber optic 215 flexes and causes position dependencies. Further, as the apparatus shown in FIG. 2b moves in the x-axis direction, optical path lengths within the movable optical system are changing, which leads to position dependencies because of less than perfect collimation. Left unaccounted for or otherwise uncorrected, such position dependencies lead to inaccurate measurement results. However, if improved calibration techniques free the results from position-dependent variations and other information pertaining to the measurement system, the accuracy of the measurements can approach the precision of the tool.

Supposing that detectors 230 and 240 in FIG. 2a are sensitive to incident light with intensity, I, in a direct manner, one can express a physical model of a detector signal, S, as:

S=(signal when light source is off)+(signal due to light from the source that has interacted with the test article)+(signal due to light from the source that has not interacted with the test article) (Eqn. 4)

In Eqn. 4, the detector signal with the light source turned off or shuttered is, the dark signal. Depending on the design of the instrument, the dark signal may be due to ambient light, leakage current generated by thermal excitation in the detector, imperfections in the double correlated sampler, or an offset voltage that is intentionally applied to the input of the analog-to-digital converter. To determine the dark signal, one blocks the light from the light source with a shutter and records a signal. Turning off the power to the light source would give the same information but it is not preferred because the stability of the light source may be affected. According to standard practices in the art, the dark signal is stored and subtracted from subsequent signals. Many commercially available detectors are thermally controlled, making the dark signal very nearly constant over time and easily removed by subtraction. The last term in Eqn. 4, so called bright background, is caused by light reflecting off the interfaces of optic components of the instrument and reaching the detector without interacting with the test article. For example, if there is a window between the test article and the instrument, light reflecting off the window can be detected. The bright background is stronger for instruments where illumination and detection beams have a common path.

A signal from reflected light detector 240, after subtracting the dark signal, may be written as:

$$S_{240}=g_{240} I_{source} [R_{250}A_{240}+(BG)_{240,R=0}]$$ (Eqn. 5)

In Eqn. 5, the first term is from light from the source that has interacted with test article 250 and then reached the detector; and the second term is the bright background. The factor $g_{240}$ in Eqn. 5 represents detector gain, which may or may not be adjustable. $I_{source}$ is the intensity of the light source and $R_{250}$ is the reflectance of the test article 250. This invention is equally applicable to a measurement where light is transmitted through the test article 250. In that case $R_{250}$ is replaced by the transmittance of test article 250. The factor $A_{240}$ in Eqn. 5 characterizes an aspect of the measurement system. It is the optical efficiency of the light path from the light source 210 interacting with the test article 250 and reaching detector 240. It may depend on geometrical factors, wavelength, and absorbance of optical components of the instrument. The factor $(BG)_{240,R=0}$ is the optical efficiency of the light path from light source 210 to detector 240 that does not interact with sample 250.

Similarly, a signal from light source monitoring detector 230 may be rewritten, with the dark signal subtracted, as:

$$S_{230} = g_{230} I_{source} A_{230} \quad \text{(Eqn. 6)}$$

In some embodiments, an entire optical system may move over a test article. In other embodiments, a subsystem may move. In embodiments including a fiber optic element, position-dependencies may arise from bending or other collateral perturbations to the fiber optic as other elements move. Moreover, such effects relating to the fiber may cause the most significant position-dependent effects. In such implementations $A_{230}$, $A_{240}$, $(BG)_{240,R=0}$ are position and wavelength dependent.

A well-known advantage of a dual beam system is that, to an excellent approximation, the intensity of light source 230, including any temporal fluctuations, may be cancelled by taking a ratio of signals from the two beams that originate at the source. This is strictly so if the ratio is formed by measurements made at the same instant, and nearly so if the ratio is formed by measurements made in quick succession. Thus, taking a ratio of signals from the two detectors:

$$\frac{S_{240}}{S_{230}} = \left(\frac{g_{240}}{g_{230}}\right)\left\{R\frac{A_{240}}{A_{230}} + \frac{(BG)_{240,R=0}}{A_{230}}\right\} \quad \text{(Eqn. 7)}$$

If detectors 230 and 240 in FIG. 2a are physically distinct detectors, gains $g_{230}$ and $g_{240}$ are not only different; they can drift differently. Taking a measurement on stable reference reflector 260 solves this problem as described in U.S. patent application No. 60/339,628 (filed Dec. 12, 2001), which is incorporated herein in its entirety by reference. If the time lapsed between the measurements of the test article and the reference reflector is sufficiently small, such as one minute or less, gains $g_{230}$ and $g_{240}$ cancel in the following ratio:

$$\frac{S_{240,sample}S_{230,reference}}{S_{240,reference}S_{230,sample}} = F_0 + RF_1 \quad \text{(Eqn. 8)}$$

$F_0$ and $F_1$ are stable properties of the instrument:

$$F_1(\lambda, r) = \frac{\left(\frac{A_{240}}{A_{230}}\right)_{sample}}{R_{reference}\left(\frac{A_{240}}{A_{230}}\right)_{reference} + \left(\frac{(BG)_{240,R=0}}{A_{230}}\right)_{reference}} \quad \text{(Eqn. 9)}$$

$$F_0(\lambda, r) = \frac{\left(\frac{(BG)_{240,R=0}}{A_{230}}\right)_{sample}}{R_{reference}\left(\frac{A_{240}}{A_{230}}\right)_{reference} + \left(\frac{(BG)_{240,R=0}}{A_{230}}\right)_{reference}} \quad \text{(Eqn. 10)}$$

The subscripts sample and reference on A and BG in Eqn. 9–10 emphasize that the sample and reference measurements may be performed at different positions. The position of the reference reflector is fixed; therefore, a quantity such as $(A_{240}/A_{240})_{reference}$ is a fixed attribute of the instrument. $F_0$ and $F_1$ depend on the position of the sample and the wavelength but they are unaffected by fluctuations in the intensity of light source 210, drift in the gains of detectors 230 and 240, or changes in sample 250. They are intrinsic and stable properties of the instrument.

Compared to many prior art techniques, accounting for the measurement system's characteristics as shown above is an improvement. Comparing Eqn. 8 to Eqn. 1, the ratio of signals from the detectors equals the surface reflectivity if and only if $F_1=1$ and $F_0=0$. Thus, ratio methods such as taught in U.S. Pat. No. 5,747,813 are not applicable when there is a bright background. In different embodiments, Eqns. 5–10 take many functional forms ranging from simple to complex. For example, multiple reflections between the sample 250 and interfaces of internal optical components of the instrument can make the instrument weakly nonlinear. Spurious light reaching from the test article to the intensity monitor 230 also causes a weak non-linearity. In that case, the right hand side of Eqn. 8 becomes $F_0+F_1R+F_2R^2+F_3R^3+...$ In preferred embodiments, at least a portion of the optical system moves over measurement points on a test article and the light source is multi-chromatic. In a preferred embodiment, a chuck rotates a test wafer and an optical head moves along a radius of the wafer, r. In alternative embodiments, an optical head moves over a test wafer surface in two dimensions. See (x, y) in FIG. 2a. Thus, in these embodiments, $F_1$ and $F_0$ in Eqn. 8 are functions of position and wavelength.

Instrument parameters $F_1$ and $F_0$ are determined by measuring calibration samples at a plurality of different positions of the optical system. The calibration samples have well-understood properties such as reflectance or film thickness. Moreover, the calibration samples span an adequate range of the property. For example, it is preferred to calibrate over the range $0 \leq R \leq 1$ for reflectivity. Thus, calibration samples typically include both highly reflective and non-reflective elements. As further described below, examples of calibration samples include surfaces of bare silicon or other elements, a total absorber such as tilted pieces of black glass or stacked razor blades, or well-defined thin film layers such as 50 nm or 100 nm thermal oxides on silicon. Typically, the calibration samples are the same size as the test articles to be measured after calibration.

The following three embodiments of the calibration method as applied to a dual beam system are convenient for illustration purposes. No limitation to these embodiments, however, is implied. Different embodiments can be developed without departing from the scope of the invention.

Embodiment A:

In a preferred embodiment, $F_1$ and $F_0$ are determined by using two calibration samples: a non-reflecting sample and a well-characterized bright calibration sample such as a bare silicon wafer:

$$F_0(\lambda, r) = \frac{S_{240}(\text{non reflecting sample})S_{230,reference}}{S_{230}(\text{non reflecting sample})S_{240,reference}} \quad \text{(Eqn. 11)}$$

$$F_1(\lambda, r) = \left(\frac{S_{240}(\text{BareSi})S_{230,reference}}{S_{230}(\text{BareSi})S_{240,reference}} - F_0\right) / R(\text{BareSi}) \quad \text{(Eqn. 12)}$$

The reflectance of the well-characterized bright calibration sample, R(Bare Si) in Eqn. 12, is calculated from known indices of refraction of the materials that make up the calibration sample.

Embodiment B:

In another embodiment, $F_1$ and $F_0$ are determined by minimizing a vector norm in an over-determined system of equations arising from Eqn. 8, or an equivalent expression. In a particular embodiment, for example, measurements of reflectivity are made at a plurality of positions of the movable optics over each of two or more calibration samples. In this embodiment, the surface reflectivity is well known over the entire surface of each calibration sample.

With two unknowns, $F_1$ and $F_0$, at each position of the movable optics, the system of equations arising from Eqn. 8 is over-determined with measurements on more than two calibration samples. The fit error, $$\chi_{cal}^2(\lambda, r) = \sum_{calib.\,sample} \left\{ \frac{S_{240,calib.\,sample}(\lambda, r)}{S_{240,reference}(\lambda)} - (R_{calib.\,sample}(\lambda, r)F_1(\lambda, r) + F_0(\lambda, r)) \frac{S_{230,calib.\,sample}(\lambda, r)}{S_{230,reference}(\lambda)} \right\}^2 \quad (\text{Eqn. 13})$$

is minimized with respect to $F_1$ and $F_0$ separately at each position r and wavelength $\lambda$. Since $F_1$ and $F_0$ are intrinsic properties of the instrument, they are the same for each sample. Eqn. 13 corresponds to minimizing $L_2$-norm of the fit error. Although many other norms such as the $L_1$-norm is possible, the $L_2$-norm is preferred because it leads to a non-iterative solution by using the standard linear least-squares technique in linear algebra. The results are two-dimensional maps of the instrument functions $F_1(\lambda, r)$ and $F_0(\lambda, r)$. The advantages of this embodiment are that there is no need for a zero-reflectance calibration sample; the inaccuracy in the knowledge of the properties of any particular calibration sample affects the calibration to a smaller extent when many calibration samples are used. A disadvantage of this embodiment is that characterizing the calibration samples over their entire surfaces and storing such information together with the calibration samples does not lead to an efficient process.

Embodiment C:

In this embodiment, calibration samples are allowed to have few unknown parameters. For example, a calibration sample that consists of a $SiO_2$ film deposited on a silicon wafer may have 5% thickness variation over the wafer. Let q denote the vector, or list, of unknown parameters of the calibration samples. Three or more calibration samples allow determination of $F_1(\lambda, r)$, $F_0(\lambda, r)$ and q by minimizing the following expression:

$$\chi_{cal}^2(\lambda, r) = \sum_{\lambda} \sum_{calib.\,sample} \left\{ \frac{S_{240,calib.\,sample}(\lambda, r)}{S_{240,reference}(\lambda)} - (R_{calib.\,sample}(\lambda, r; q)F_1(\lambda, r) + F_0(\lambda, r)) \frac{S_{230,calib.\,sample}(\lambda, r)}{S_{230,reference}(\lambda)} \right\}^2 \quad (\text{Eqn. 14})$$

$F_0$ and $F_1$ for all wavelengths and the parameters q are determined together in one minimization operation per position r. The minimization is repeated for each position. The minimization with respect to the parameters q (for example film thickness) requires non-linear least-squares minimization. An efficient algorithm minimizes $\chi_{cal}^2(r)$ in Eqn. 14 alternately with respect to q and then with respect to $F_0$ and $F_1$. The reason this algorithm is efficient is that for fixed q, the minimization with respect to $F_0$ and $F_1$ is a linear algebra problem that does not require iteration. For fixed $F_0$ and $F_1$, minimization with respect to q uncouples for each sample, i.e., the parameters of each sample can be updated independently of the others. The Levenberg-Marquardt algorithm is preferred for minimizing $\chi_{cal}^2(r)$ with respect to q. Many other non-linear least-squares algorithms are possible. The algorithm then updates $F_0$ and $F_1$ by the linear least-squares method holding q fixed; and then updates q holding $F_0$ and $F_1$ fixed; and so on. The results of the minimization are two-dimensional maps of $F_1(\lambda, r)$, $F_0(\lambda, r)$ and the maps of parameters q(r) over the parts of the calibration wafers that are scanned. This embodiment is most complex in computation but it leads to the most practical calibration process.

A zero-reflectance sample is not required. The thickness of the films on the calibration samples need not be known. All that is required of the calibration samples are that they are sufficiently distinct from each other, and their optical response is accurately represented by a model that has few adjustable parameters.

As described above, the primary results of the minimization are maps of $F_1(\lambda, r)$ and $F_0(\lambda, r)$ over discreet sets of wavelengths and positions. In subsequent measurements, the values of the instrument calibration functions are needed at other positions and wavelengths. In that case, the calibration functions $F_1(\lambda, r)$ and $F_0(\lambda, r)$ are interpolated from the stored discreet values. In a preferred embodiment, polynomials are fitted to $F_1(\lambda, r)$ and $F_0(\lambda, r)$:

$$F_j(\lambda, r) = a_{j0}(\lambda) + a_{j1}(\lambda)r + a_{j2}(\lambda)r^2 + \ldots + a_{jN}(\lambda)r^N + \ldots; j=1,2 (\text{Eqn. 15})$$

where the degree of the polynomial, N, is typically less than 10. Eqn. 15 treats r as a single variable. The polynomial in Eqn. 15 is replaced by a two-dimensional polynomial if the stage position r=(x, y) is two-dimensional. A separate set of polynomial coefficients are calculated at each wavelength. The advantage of this approach is that outliers due to particles on the window are flagged as poorly fitting points in the polynomial fit. Another advantage is that only polynomial coefficients need be stored. This takes less storage compared to storing discreet values of $F_1(\lambda, r)$ and $F_0(\lambda, r)$. Many other embodiments such as spline fits are possible.

Once the measurement system is characterized by knowledge of $F_0$ and $F_1$, the information can be used to account or correct for position-dependencies when measuring test articles with unknown physical properties. Eqn. 8 may be used to solve for reflectance of test articles, with $F_0$ and $F_1$ as known quantities:

$$R_{test}(\lambda, r) = \qquad (\text{Eqn. 16})$$
$$\left( \frac{S_{240,test}(\lambda, r) S_{230,reference}(\lambda, r_{ref})}{S_{240,reference}(\lambda, r_{ref}) S_{230,test}(\lambda, r)} - F_0(\lambda, r) \right) \bigg/ F_1(\lambda, r)$$

Parameters $q_{test}$ of the test article can be determined by minimizing the fit error $$\chi_{test}^2 = \sum_{\lambda} \{R_{test}(\lambda, r) - R_{model}(\lambda; q_{test})\}^2 W^2(\lambda) \qquad (\text{Eqn. 17})$$

In Eqn. 17, $R_{model}(\lambda; q_{test})$ is a computational model of the optical response of the test article with adjustable parameters $q_{test}$. The weighting function $W^2(\lambda)$ is used to maximize the repeatability of the estimates of $q_{test}$. Preferably, $W^{-2}(\lambda)$ is the statistical variance of $R_{test}(\lambda)$. The search for a minimum goes according to any of several well-known algorithms, such as the Levenberg-Marquardt algorithm. As in the calibration, a variety of vector norms may be used in different embodiments, such as the $L_1$-norm. In preferred embodiments, the calculated $R_{mod\ el}(\lambda; q_{test})$ accounts for the numerical aperture and the point-spread-function of the spectrometer used in the instrument.

II. Chuck and Wafer with Calibration Reference Portions

The present invention is a calibration method suitable for highly precise and highly accurate surface metrology measurements. The method typically includes taking measurements of a non-reflective calibration reference over a plurality of positions of a movable optical system. With a non-reflective calibration reference, detector signals can measure background light arising from spurious reflections, scattering, and other mechanisms.

As described above, the movable optical system typically has a head portion with a scanning range including all locations where metrology measurements are to be made on a test article. In preferred embodiments, the optical head of the instrument scans in one dimension, r, and the test article is a wafer held by a chuck that rotates by an angle θ, allowing measurements to be made at different locations over the wafer.

Figure 3:
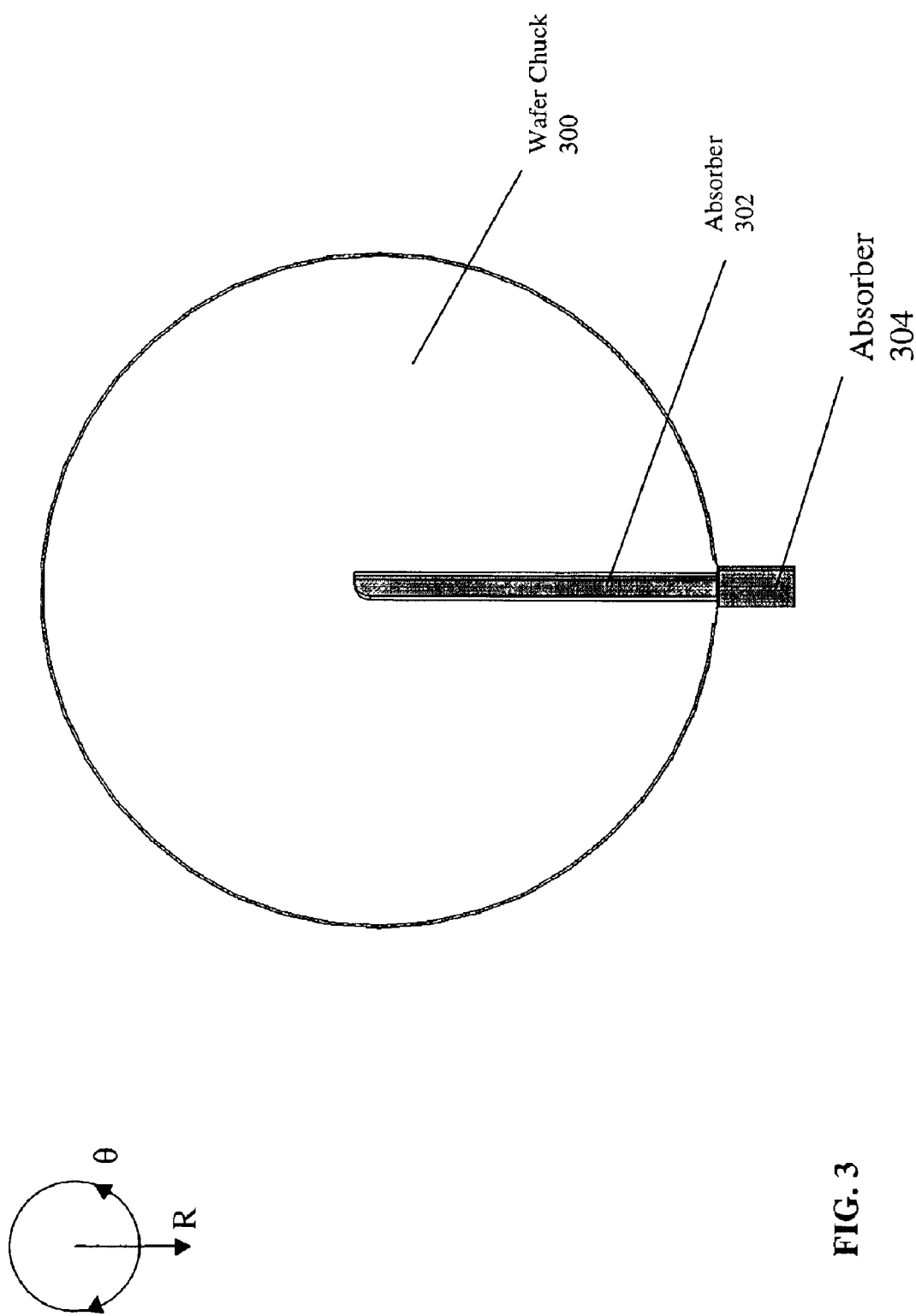
FIG. 3 illustrates a top view of a chuck with a non-reflective radial portion.
Figure 4:
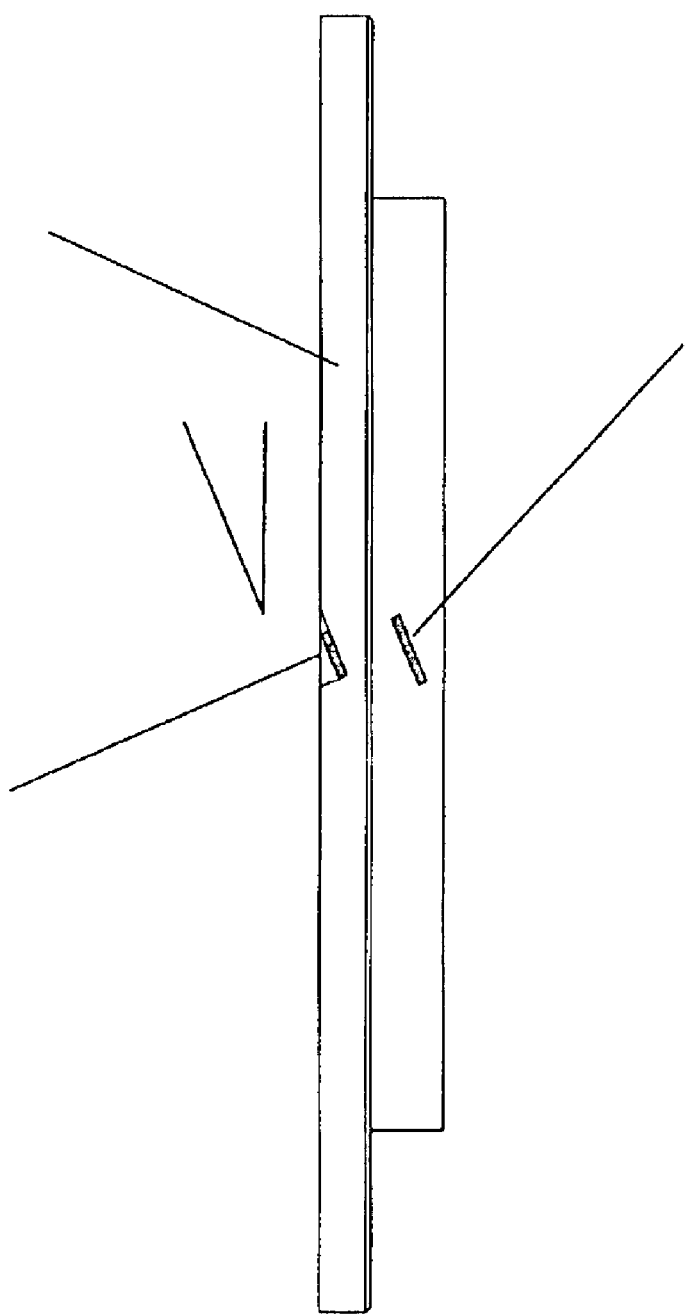
FIG. 4 illustrates a cross section of a chuck with a tilted absorber portion.

Referring to FIG. 3, absorber 302 is one or more non-reflective strips embedded into chuck 300 preferably covering at least an area along a radius. The absorber is fixed relative to a center of mass of the chuck. As shown in cross-section in FIG. 4, the absorber comprises a rectangular prism of "black glass" 402, for example Schott NG1 glass, which has tilt 403 with respect to the surface of chuck 400 so that it's top surface is not horizontal. The black glass generally has a highly polished top surface. The black glass and the chuck are secured together with an adhesive suitable for use in microelectronics applications, for example 3M Scotch-Weld Epoxy DP 190 Grey. The tilt is approximately 20° to ensure that the collection optics of the metrology unit does not collect the Fresnel reflection from the surface of the glass. Typically, the movable collection optics have numerical aperture (NA) of 0.28 (viz., rays spreading out to 16.26° from a normal to the chuck). This design is suitable for other embodiments having smaller numerical apertures.

For a thorough calibration, it is preferred to have the absorber accessible over the entire range of motion of the optical head. Absorber 302 embedded in chuck 300, however, cannot completely lie within the range of motion of the optical head because the chuck's dimensions are often smaller than the dimension of the test article. See FIG. 3. Therefore, extension absorber 304 extends beyond the chuck surface out to a full radius of a test wafer. Typically, the movable optics scan at least that far.

In FIG. 3, extension absorber 304 can be any kind of absorber. In a preferred embodiment, the extension absorber is made of the same materials and to the same shape as absorber 302, which is embedded in chuck 300. In alternative embodiments, however, the extension absorber may differ in material or structure.

Figure 5:
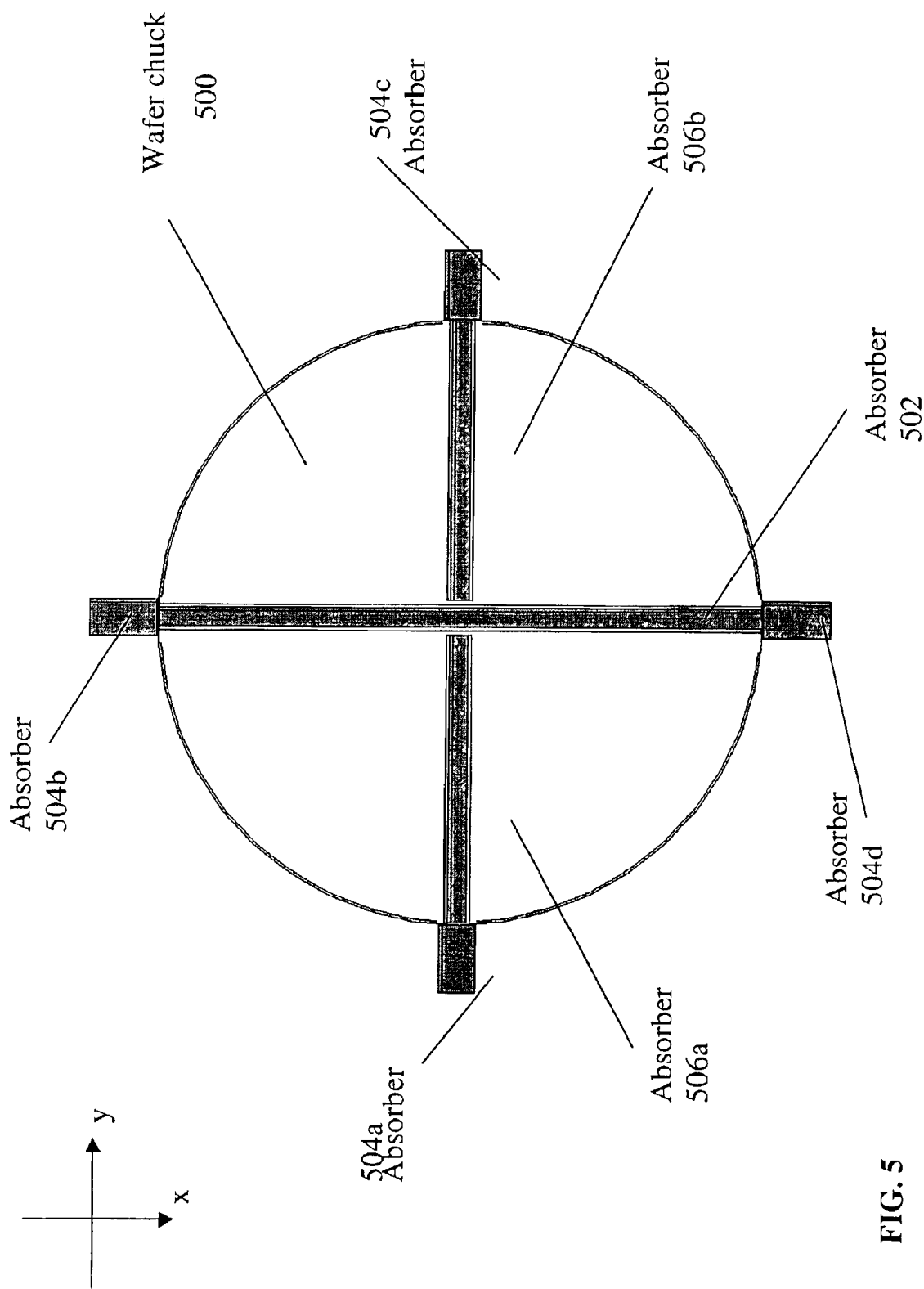
FIG. 5 illustrates a top view of a chuck with non-reflective crossed portions.

In an alternative embodiment, the optical head of the metrology instrument scans in two dimension, (x, y), to make measurements at different locations on a test article. In this case, referring to FIG. 5, the absorber consists of 'x' strip 502 that is continuous along a diameter of chuck 500 in the x direction and 'y' strips 506a and 506b that nearly cover an orthogonal diameter of the chuck, and optional extension absorbers 504a–d. The optical background signal along the x-axis can be measured by moving the optics in the x direction along the diameter of the chuck and beyond if appropriate. The optical background signal along the y-axis can be measured by moving the optics along the strips oriented in the y direction and beyond if appropriate.

In alternative embodiments, calibration samples other than the absorbing sample are coupled to the chuck. For example, in FIG. 5, strip 502 can be absorbing strip, strip 506a can be bare silicon, and strip 506b can be an oxide film on a silicon substrate. Calibration samples other than an absorbing strip are preferably not tilted. Rather, their surfaces are parallel to the plane of the chuck and the surface of the test article. Strips 502, 506a, 506b may be scanned radially by the moving optics one at a time by rotating the chuck so that the calibration strip that is being measured is aligned with a radial translation means of the instrument. In some embodiments, calibration samples coupled to the chuck are recessed from the surface of the chuck so that they do not interfere with the test article. Further, different z-positions (height) of non-absorbing calibration samples may require changing the focus of the optical instrument in different embodiments by either lowering or raising the chuck or the optics. Changing the focus is typically not required for the absorbing strip because negligible light returns from the absorbing sample even if the sample is not in focus.

In alternative embodiments, the movable optical head can scan in two dimensions and the chuck can be rotated. In this case, referring to FIG. 6, the absorber comprises horizontal strip 602 that is continuous along a diameter of chuck 600 and optional non-rotating extension absorbers 604a–d. The optical background signal across the x-axis is measured by rotating the chuck so that absorber 602 lies along an x diameter of the chuck. See FIG. 6. Then, the optics move along in x along the diameter, and beyond if appropriate. The optical background signal across the y-axis is measured by rotating absorber 602 to a position covering the y diameter of the chuck (not shown); then moving the optics in y along the diameter and beyond if appropriate.

Figure 7:
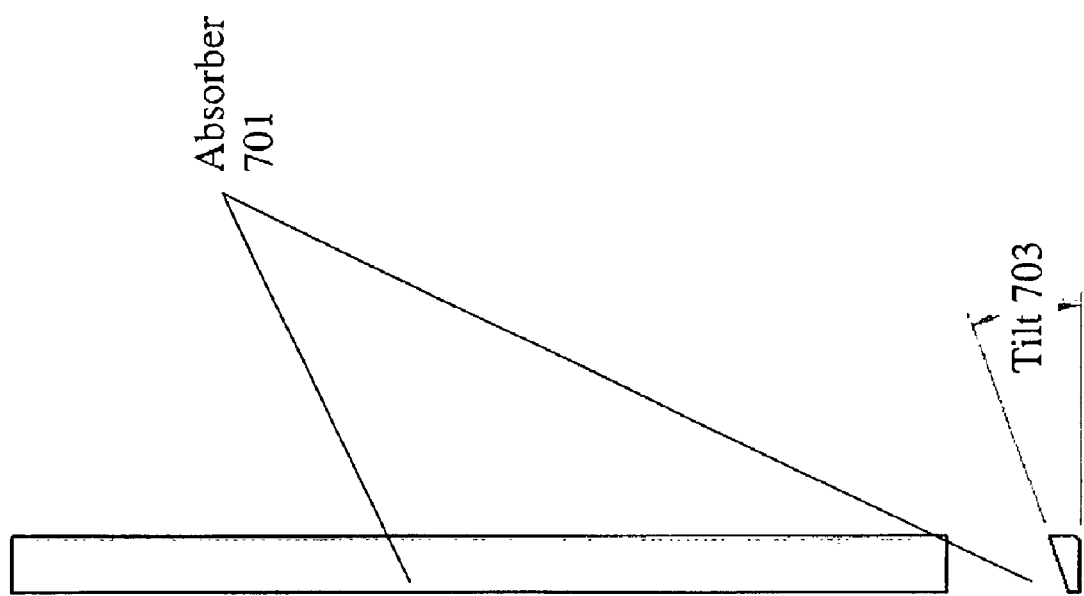
FIG. 7 illustrates an alternative embodiment of a chuck with non-reflective portions.

FIG. 7 illustrates a preferred embodiment in top view and cross-section. Absorber 701 has a cross-section that facilitates mounting on a horizontal while maintaining low reflection back into the collection optics. Accordingly, the top surface is polished, and has a tilt 703 of about 20°0 that ensures that Fresnel reflections are directed away from the collection optics, which in one embodiment has a NA of 0.28.

Figure 8:
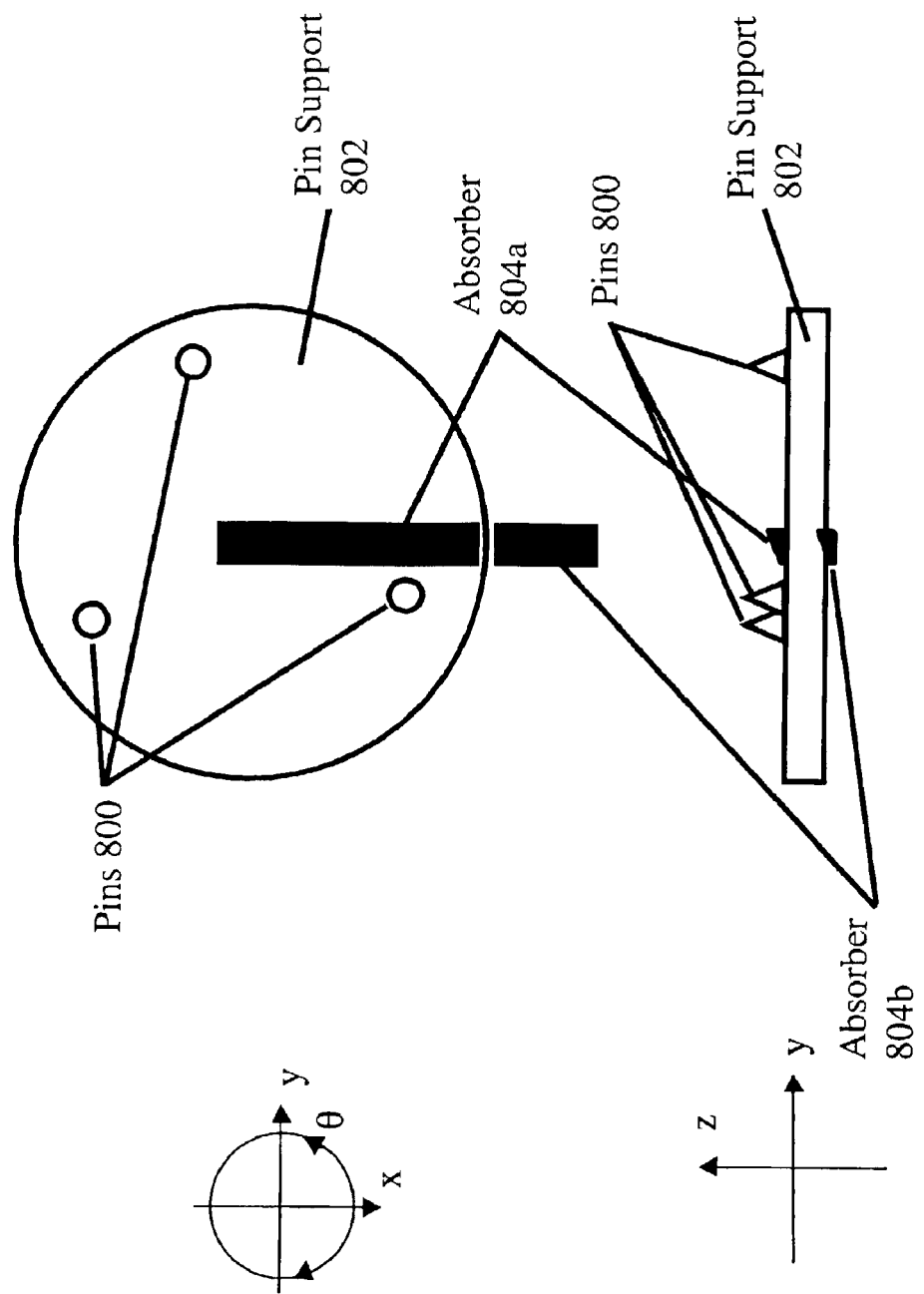
FIG. 8 illustrates an alternative embodiment of a chuck with pin supports.

FIG. 8 shows an alternative embodiment. In FIG. 8, a rotating three-pin support for a wafer is shown from the top and from the side. Pins 800 are mounted to rotating pin support 802. Rotating absorber 804a covers substantially an entire radius of pin support 802. Fixed absorber 804b extends the radius covered by absorber 804a to substantially the maximum radius of use of the optical system, viz. roughly a wafer radius. The chassis of the metrology instrument (not shown) supports both pin support 802 and fixed absorber 804b.

As an alternative to being mounted on a chuck, the non-reflective calibration reference may be coupled to a calibration wafer. However, for integrated metrology applications, a calibration wafer with a non-reflective portion may be less desirable than a chuck as described above because such a wafer may be unsuited for standard handling equipment, or may introduce particles into the process environment.

Figure 9:
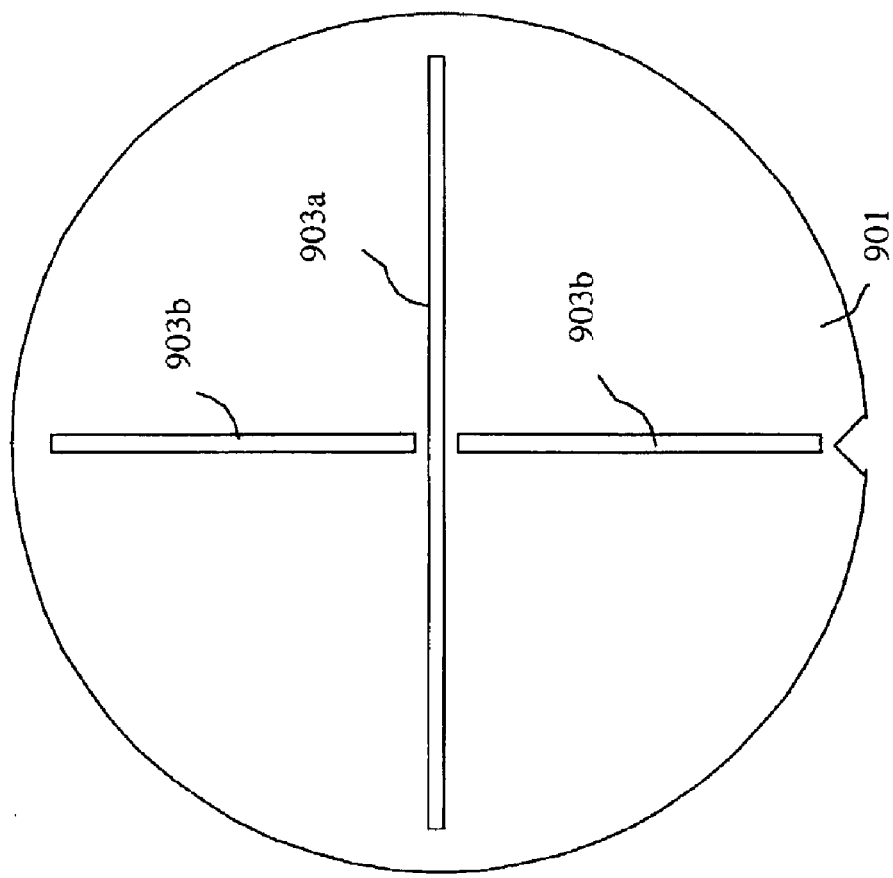
FIG. 9 illustrates a top view of a wafer with non-reflective portions.
Figure 10:
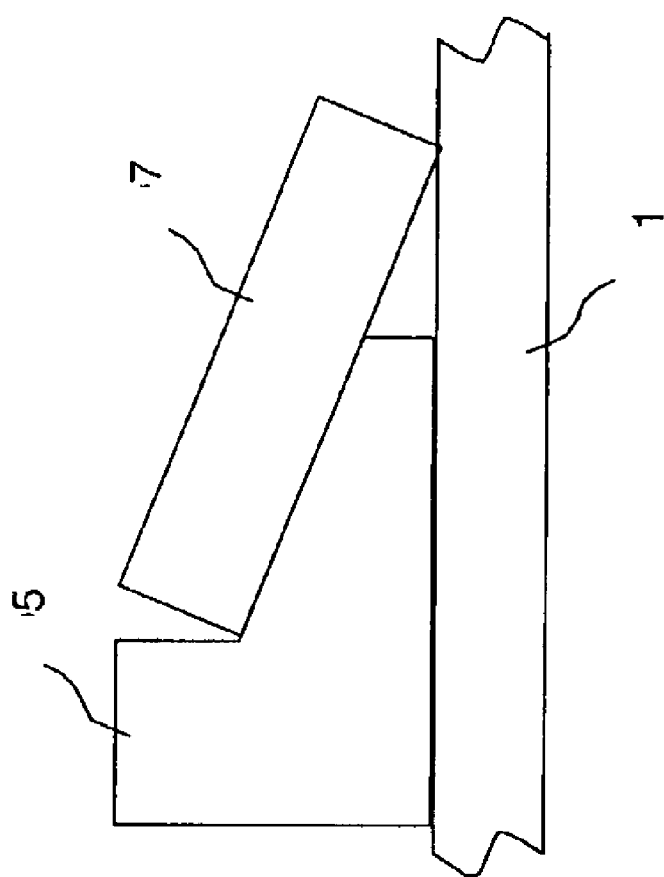
FIG. 10 illustrates a cross section of a wafer with a tilted absorber portion.

When on a wafer, black glass is arrayed and secured as shown in FIG. 9 and FIG. 10, respectively. In a preferred embodiment, wafer 901 is a 200 mm silicon wafer that has been processed with patterns on its top surface suitable for pattern recognition. In FIG. 9, non-reflective strips 903a–b cover the wafer. In a preferred embodiment, horizontal strip 903b is continuous along a diameter of the wafer, and vertical strips 903b nearly cover an orthogonal diameter of the wafer. In FIG. 10, a cross-section shows black glass 1007 coupled to wafer portion 1001 by support 1005. Typically, the support is made of black anodized aluminum. The black glass is generally in the shape of a rectangular prism, with a highly polished top surface. The support, black glass and wafer are all adhered together with an adhesive such as 3M Scotch-Weld Epoxy DP 190 Gray. As with the chuck embodiments, a roughly 20° tilt ensures that Fresnel reflections from the surface of the black glass do not go back into the optical system. Other embodiments of a non-reflective wafer are possible. For example, the wafer may be composed of carbon fiber or another durable and clean material.

III. Working Example

In the preceding description, a dual beam optical system for determining surface reflectivity illustrated several embodiments of the invention. The invention, however, is not limited to the above illustrations. The following working example refers to single beam embodiments, such as described in U.S. patent application No. 10/290,730, filed Nov. 7, 2002, which is incorporated in its entirety by reference.

In this example, the single beam system differs from the dual beam system illustrated in FIG. 2a primarily in that light source monitoring detector 230 is replaced by a beam dump, or trap. In order to monitor light source 210, the single beam system uses a movable mirror that alternately flips in and out of the optical path between beam splitter 220 and reflective surface 250. As compared to a dual beam system where two signals are obtained simultaneously, the single beam approach collects two signals in a sequence. First, the movable mirror is in the optical path and detector 240 sees light source 210. Then, the mirror moves out of the optical path, allowing the detector to see the reflective surface. If the light source is relatively stable over the time of the measurement sequence, the single beam system reduces the cost of detectors and associated optics by 50% with little accuracy loss.

In typical embodiments, the light source includes a broadband spectral lamp coupled to an optical fiber and collimating lenses. Reflected light detector 240 is typically a solid-state array detector, such as a diode array or a charge-coupled device (CCD) array, coupled to a spectrograph.

In the following, reflective surface 250 is a calibration wafer held by a rotatable chuck having non-reflective portions. See FIG. 2a and FIG. 6. As shown, movable optical system 200 translates. By combining a translation and a rotation, the optical system has access to any point $(r,\theta)$ on the wafer surface. The translation, however, introduces significant position-dependant effects. As the optical system moves from position to position to access different points on the wafer, associated elements such as optical fibers, lenses, and mirrors move. For some elements, the motion is a small perturbation. However, for optical fibers in particular, the motion involves substantial flexing. Thus, as a direct result of the motion of the movable optical system, the behavior of the measurement system is position-dependent and requires careful characterization. Common calibration steps such as correcting for dark current or scattering within a spectrometer are insufficient. Data from test wafers with unknown properties can be interpreted accurately only after the position-dependencies are accounted for, or otherwise corrected.

In an exemplary embodiment, a calibration proceeds as follows. First, movable optical system 200 is positioned over reference reflector 260. A dark spectrum is recorded after first closing a shutter; then a lamp monitor spectrum is recorded with the shutter open and a mirror positioned between beam splitter 220 and the reference reflector. A dark-corrected spectrum is calculated immediately. In certain embodiments, one or more pixels at an end of the array detector also measure the diffuse scattering in the spectrometer for subtraction. The mirror is then removed from the optical path and, a short time after the lamp monitor spectrum is collected, the preceding steps are repeated to measure the light reflected back from the reference reflector. The spectra from the lamp and the reference reflector are stored for further use.

Second, movable optical system 200 is positioned over chuck 600, which has non-reflective portions. See FIG. 6. Following a schedule, data are serially collected at a plurality of positions over a range of motion of the optical system. Typically, the optical system moves a few millimeters between calibration positions. The data collection at each calibration position is as described in the preceding paragraph. A dark spectrum is collected, followed by a spectrum with a mirror in the optical path. The process is repeated in quick succession with the mirror out of the optical path. Scattering in the spectrometer is also recorded for subtraction. Then, the optical system moves on to a new position until the schedule of positions is finished.

Third, one or more calibration references are measured in a series. A calibration reference is placed on the chuck 600 and, following a schedule and the procedure as above, data are collected at a plurality of positions over the chuck. As described, the range of motion may be less than in the case of measuring over the non-reflective portions of the chuck.

After the number of independent measurements on the calibration references and the non-reflective chuck portions are sufficient in number to adequately determine the mathematical problem, the optical system moves to the reference reflector again and repeats the earlier measurements.

Typically, enough data are collected to over-determine the mathematical solution of the calibration problem. The data, along with the known physical quantities of the calibration references and non-reflective chuck portions, are inputs to minimizing Eqn. 13, or Eqn. 14, or Eqn. 17, or an equivalent, over discreet sets of wavelengths and positions. The result of the minimization is $F_1(\lambda,r)$ and $F_0(\lambda,r)$, as discreet maps at the calibration wavelengths and points. In subsequent measurements, the values of the instrument calibration functions are needed at other positions and wavelengths. Therefore, the calibration functions $F_1(\lambda,r)$ and $F_0(\lambda,r)$ at those points are interpolated from the stored discreet values. In preferred embodiments, however, continuous functions are fitted to the discreet map for $F_0$ and $F_1$. The continuous fits to the discreet calibration results for $F_1(\lambda,r)$ and $F_0(\lambda, r)$ are then stored for use in interpreting data taken from test articles with unknown properties.

Measurements on the test articles, or wafers, proceed as described above for the calibration references. Once data are collected, they can be interpreted according to Eqn. 13, or Eqn. 14, or Eqn. 17, or equivalents. In these calculations, however, $F_1(\lambda,r)$ and $F_0(\lambda,r)$ are known by the calibration maps themselves or the fits, and the minimization problem varies quantities that relate to the wafer under test. The results in terms of reflectivity or film thickness are free of position-dependent variations and other information pertaining to the measurement system. Thus, the accuracy of the wafer measurement can approach the precision of the tool.

It should be appreciated that in accordance with the subject technique, calibration information is measured and stored as a function of both position and wavelength. This calibration information at individual wavelengths and positions is then used to improve the measurement. In an earlier prior art version of the tool manufactured and sold by the assignee herein, calibration information was measured as a function of position but the wavelength information was merely summed or integrated and stored. No attempts were made to calibrate the system based on a combination of independent wavelength and independent position information.

As is readily apparent to a skilled person, the invention is not limited to the above-described embodiments. Rather, different configurations and embodiments can be developed without departing from the scope of the invention and are intended to be included within the scope of the claims set forth below. Moreover, instructions for the full scope of method embodiments may be inscribed according to well-known techniques onto tangible articles of manufacture, including but not limited to magnetic disks and tapes; optical disks; and non-volatile memory chips. When executed by a computer processor, the instructions cause a computer to perform the methods.

We claim:

1. A method, comprising:
moving a portion of an optical metrology apparatus over a plurality of positions relative to a test article holder, whereby a measurement location over the test article holder is changed;
producing calibration signals over the plurality of positions with the optical metrology apparatus, the calibration signals containing information over a range of wavelengths; and
determining values for position-dependant parameters characterizing the optical metrology apparatus at a plurality of discreet wavelength values based on the calibration signals.

2. The method of claim 1, further comprising:
generating signals with the optical metrology apparatus and a test article, the signals containing information about the optical metrology apparatus and a physical characteristic of the test article over a range of wavelengths; and
determining the physical characteristic of the test article from the signals by interpreting the signals with any of the position-dependant parameters.

3. The method of claim 2, wherein determining the physical characteristic of the test article from the signals includes interpreting the signals with all of the position-dependant parameters.

4. The method of claim 1, wherein moving a portion of an optical metrology apparatus includes changing an optical path length within the optical metrology apparatus.

5. An apparatus, comprising:
a chuck with a support structure upon which a test article rests during measurement of the test article;
a metrology unit including movable optics, the metrology unit positioned relative to the chuck such that, over a range of travel, the movable optics have optical access to a surface of the test article; and
at least one calibration reference fixed to a chuck portion, wherein the calibration reference is an absorber.

6. The apparatus of claim 5, wherein the chuck is fixed.

7. The apparatus of claim 5, wherein the chuck is configured to rotate about an axis.

8. The apparatus of claim 5, wherein the metrology unit is a member of a set of metrology units consisting of: reflectometers; ellipsometers; scatterometers; and profilometers.

9. The apparatus of claim 5, wherein the absorber is black glass.

10. The apparatus of claim 5, wherein the absorber is a reflective light trap.

11. The apparatus of claim 5, wherein the test article held by the chuck is interposed between the entire at least one calibration reference and the movable optics.

12. The apparatus of claim 5, wherein a linear extent of the at least one calibration reference matches at least a portion of the range of travel of the movable optics.

13. The apparatus of claim 5, wherein the calibration reference is positioned such that the test article is interposed between a portion of the at least one calibration reference and the movable optics when the test article rests on the support structure.

14. An apparatus, comprising:
a chuck with a support structure upon which a test article rests during measurement of the test article;
a metrology unit including movable optics, the metrology unit positioned relative to the chuck such that, over a range of travel, the movable optics have optical access to a surface of the test article; and
at least one calibration reference fixed to a chuck portion, wherein the calibration reference is an absorber;
wherein the absorber is coupled to the chuck such that at least one surface of the absorber is tilted with respect to an optical axis of the movable optics.

15. An apparatus, comprising:
a chuck with a support structure upon which a test article rests during measurement of the test article;
a metrology unit including movable optics, the metrology unit positioned relative to the chuck such that, over a range of travel, the movable optics have optical access to a surface of the test article; and
at least one calibration reference fixed to a chuck portion, wherein the calibration reference is an absorber, the absorber being a reflective light trap;
wherein the reflective light trap comprises a series of razor edges.

16. A method, comprising:
moving a portion of an optical metrology apparatus over a plurality of positions relative to a wafer chuck, whereby a measurement location over the wafer chuck is changed;
producing calibration signals over the plurality of positions with the optical metrology apparatus and a calibration reference fixed to the wafer chuck, the calibration signals containing information over a range of wavelengths;
placing a calibration wafer on the wafer chuck;
producing calibration signals over the plurality of positions with the optical metrology apparatus and the calibration wafer, the calibration signals containing information over a range of wavelengths; and
determining values for position dependant parameters characterizing the optical metrology apparatus at a plurality of discreet wavelength values based on the calibration signals.

17. The method of claim 16, wherein producing calibration signals includes serially placing more than one calibration wafer on the wafer chuck.

18. An apparatus, comprising:
a chuck with a support structure upon which a test article rests during measurement of the test article;
a metrology unit including movable optics, the metrology unit positioned relative to the chuck such that, over a range of linear travel, the movable optics have optical access to a surface of the test article; and a calibration reference fixed to the chuck, said calibration reference extending along the linear range of travel of the movable optics.

19. The apparatus of claim 18, wherein the calibration reference is an absorber.

20. The apparatus of claim 19, wherein the absorber is black glass.

21. An apparatus, comprising:

a chuck with a support structure upon which a test article rests during measurement of the test article;

a metrology unit including movable optics, the metrology unit positioned relative to the chuck such that, over a range of linear travel, the movable optics have optical access to a surface of the test article; and a calibration reference fixed to the chuck, said calibration reference extending along at least a portion of the linear range of travel of the movable optics;

wherein an absorber is coupled to the chuck such that the at least one surface of the absorber is tilted with respect to an optical axis of the movable optics.

* * * * *